(12) United States Patent
Sakal et al.

(10) Patent No.: US 7,494,472 B2
(45) Date of Patent: Feb. 24, 2009

(54) DUCTAL LAVAGE CATHETER HAVING AN OFF-AXIS TIP

(75) Inventors: Robert Sakal, Bolton, MA (US); Ellen E. Sheets, Concord, MA (US); Meghan Brennan, Newburyport, MA (US); Greg R. Furnish, Louisville, KY (US); Charles H. Whatley, Jr., Louisville, KY (US); Ben E. Morris, Louisville, KY (US); Indi Gunasekara, Louisville, KY (US)

(73) Assignee: Windy Hill Medical, Inc., Laguna Hills, CA (US)

( * ) Notice: Subject to any disclaimer, the term of this patent is extended or adjusted under 35 U.S.C. 154(b) by 1134 days.

(21) Appl. No.: 10/746,950

(22) Filed: Dec. 23, 2003

(65) Prior Publication Data

US 2005/0137524 A1 Jun. 23, 2005

(51) Int. Cl.
*A61B 10/00* (2006.01)
(52) U.S. Cl. ...................... 600/562; 600/563
(58) Field of Classification Search .................. 600/56, 600/563, 573; 604/105, 106, 158, 164.01, 604/164.04, 164.05, 164.1, 164.11, 164.13, 604/166.01
See application file for complete search history.

(56) References Cited

U.S. PATENT DOCUMENTS

| 5,662,585 | A | * | 9/1997 | Willis et al. ............... 600/104 |
| 5,735,792 | A | * | 4/1998 | Vanden Hoek et al. ...... 600/138 |
| 5,746,692 | A | * | 5/1998 | Bacich et al. ............... 600/104 |
| 6,500,114 | B1 | * | 12/2002 | Petitto et al. ............... 600/156 |
| 2005/0027236 | A1 | * | 2/2005 | Douk ......................... 604/40 |

* cited by examiner

*Primary Examiner*—Max Hindenburg
*Assistant Examiner*—Jonathan M Foreman
(74) *Attorney, Agent, or Firm*—Knobbe, Martens, Olson & Bear, LLP (57) ABSTRACT

A ductal access device is provided for accessing a breast duct and collecting biological material from within the duct. The access device may include an elongated member having an outer diameter sized for positioning within the breast duct and an internal lumen for infusing a fluid into the breast duct and collecting fluid from the breast duct. The elongated member may include a central axis extending through the internal lumen and a different axis being parallel to the central axis defining an off-axis configuration. An elongated distal tip extends beyond the distal end of the internal lumen and along the different axis. The elongated distal tip has a closed distal end for navigating within the breast duct. The elongated distal tip may include an internal passageway that is sized to slidiably or removably receive an elongated introducer.

19 Claims, 9 Drawing Sheets

| GUIDE WIRE/INTRODUCER MATERIALS | DIAMETER (INCH) | DIAMETER (INCH) | DIAMETER (INCH) | DIAMETER (INCH) |
|---|---|---|---|---|
| STAINLESS STEEL WIRE | 0.01 | | | |
| FEP | 0.008 | 0.01 | 0.013 | 0.015 |
| PTFE | 0.01 | 0.012 | 0.015 | |
| PEEK | 0.008 | 0.01 | 0.012 | 0.013 |
| PVDF | 0.01 | 0.012 | 0.015 | |
| Pebax | | | | |

FIG. 11

| CANULA MATERIALS | I.D. x O.D. (INCH) | I.D. x O.D. (INCH) | I.D. x O.D. (INCH) | I.D. x O.D. (INCH) |
|---|---|---|---|---|
| POLYCARBONATE | 0.024 x .036 | | | |
| STAINLESS STEEL WIRE (300 SERIES) | | | | |
| POLYIMIDE | | | | |
| FEP | | | | |
| PTFE | .010 x .028 | .012 x .030 | .013 x .030 | .019 x .038 |
| PEEK | .010 x .022 | .011 x .025 | .012 x .030 | |
| POLYETHYLENE | .011 x .025 | .015 x .043 | | |
| Pebax | .010 x .018 | .013 x .020 | | |

DUCTAL LAVAGE CATHETER HAVING AN OFF-AXIS TIP

FIELD OF THE INVENTION

Aspects of the present invention are directed generally to systems and methods for accessing an opening of a body orifice, such as a breast duct. Specifically, aspects of the present invention relate to a catheter having an off-axis tip for accessing a breast duct.

BACKGROUND OF THE INVENTION

The breast is a specialized, glandular structure including a system of complicated breast ducts that radiate from the nipple and that are bound together by fairly dense connective tissue. Each of these breast ducts includes an associated ductal orifice on the surface of a nipple through which ductal fluid may be expressed. Each duct includes a series of successive interlobular branches that drain through the main, lactiferous branch, which terminates and exits the breast at the nipple via the associated ductal orifice. Immediately proximate the ductal orifice, each lactiferous duct includes a lactiferous sinus in which ductal fluid may accumulate. A ductal sphincter resides within the lactiferous sinus and prevents ductal fluid from unintentionally exiting the breast duct through its associated ductal orifice.

Breast cancer is believed to begin in the lining of these breast ducts. For several decades significant members of the medical community dedicated to studying breast cancer have believed and shown that the cytological analysis of cells retrieved from nipple discharge fluid from within breast ducts may provide valuable information leading to identifying patients at risk for breast cancer. Indeed, Papanicolaou contributed to the genesis of such a possibility of a "Pap" smear for breast cancer by analyzing the cells contained in nipple discharge. More recently, cancer specific markers have been detected in ductal fluid obtained by nipple aspiration. However, the retrieval techniques and instruments used by these members of the medical community did not routinely obtain meaningful ductal fluid samples.

In their attempts to retrieve the breast duct fluid sample including ductal epithelial cells, practitioners introduced wash fluids into a breast duct using indwelling hair-like single lumen catheters. After the fluid was introduced into the duct, the fluid introduction catheters were removed. Then, externally applied nipple aspiration techniques or external pressure applied to the breast were used to collect samples of the ductal fluid. However, these techniques required that significant, sometimes painful, pressure be created on the nipple surface or along the sides of the breast to overcome the fluid retaining properties of the ductal sphincter. Also, these techniques did not routinely provide meaningful ductal fluid samples with a sufficient number of ductal epithelial cells for a meaningful cellular analysis. These techniques typically caused the recovery of samples with twenty or fewer ductal epithelial cells.

Additionally, these techniques did not provide samples with cell clusters of 10 or more cells. As a result, the obtained fluid samples could not consistently provide an accurate indication of whether or not the duct from which they were retrieved included precancerous or cancerous cells. Consistent, meaningful ductal epithelial cell samples have been provided by the medical instrument disclosed in U.S. Pat. No. 6,413,228 to Hung et al. that is hereby incorporated by reference in its entirety.

The human breasts are composed of fatty tissue, fibrous tissue, breast ducts and milk glands. Human breasts are believed to contain from 6 to 8, or more breast ducts. The ductal lavage procedure discussed above, and sampling results may be greatly effective in screening patients for an early warning of breast cancer risk. However, in performing the ductal lavage procedure, a physician may have difficulty inserting the catheter into a breast duct. The breast duct is a complex anatomical pathway to the breast milk glands. The physician must access the breast duct so as not to cause damage to the inner walls of the duct and/or avoid puncturing the duct. However, it is believed the deeper a catheter is inserted into breast duct, the greater the risk of puncturing the breast duct walls. Therefore, a need exists for a ductal access catheter that allows the physician to adjust its flexibility and rigidity so as to adapt the catheter to the ductal geometry and direct the catheter deep into branches of the ductal network.

During the ductal access procedure, a catheter is inserted into a duct opening in the nipple that may cause some discomfort to the patient. Thus, improved insertions systems and methods for ductal access are needed.

SUMMARY OF THE INVENTION

Aspects of the present invention pertain to systems and methods for intraductal access and navigation, including a catheter having different ductal tip configurations.

In accordance with one aspect of present invention, an elongated member sized for positioning within a breast duct is provided. The elongated member includes an elongated internal lumen extending along a length of the elongated member and an elongated internal pathway extending along at least a portion of the length of the elongated member for receiving an introducer. The elongated member includes a central longitudinal axis positioned and extending within the internal lumen. The elongated internal passageway includes a centrally disposed longitudinal axis that is spaced from and offset from the central longitudinal axis; and the elongated member includes an elongated distal tip extending beyond a distal end of the internal lumen and along the longitudinal axis.

In another aspect of the present invention, a ductal access device for accessing a breast duct and collecting biological material from within the duct is provided. The access device includes an elongated member having an outer diameter sized for positioning within the breast duct and an internal lumen for infusing a fluid into the breast duct and collecting fluid from the breast duct. The elongated member includes a central axis extending through the internal lumen and a different axis being parallel to the central axis defining an off-axis configuration. An elongated distal tip extends beyond the distal end of the internal lumen and along the different axis. The elongated distal tip has a closed distal end for navigating within the breast duct.

In yet another aspect of the present invention, a ductal access system for accessing a breast duct and collecting biological material from within the duct is provided. The access system includes a cannula having an outer diameter sized for positioning within the breast duct and an internal lumen for infusing a fluid into the breast duct and collecting fluid from the breast duct. The cannula has a central axis extending through the internal lumen and a second axis that is parallel to the first axis so as to define an off axis arrangement. An elongated distal member extends along the second axis and beyond the distal end of the internal lumen. The elongated distal member includes an internal passageway which is sized to slidably or removably receive an elongated introducer. A multiport hub body is attached to the proximal end of the internal lumen and operatively communicated with the internal lumen of the cannula for infusing fluid into the breast duct and for retrieving fluid from the breast duct.

In still another aspect of the present invention, a method for obtaining cellular material from a human breast milk duct using a ductal access device is provided. The method includes the steps of inserting a ductal introducer into an internal passageway of the elongated distal member to form a composite insertion member; inserting the composite insertion member into a ductal orifice of the breast duct; and advancing the internal lumen into the breast duct.

The above and other aspects, features and advantages of the present invention will be readily apparent and fully understood from the following detailed description illustrative embodiments in conjunction with the accompanying drawings, which are included by way of example, and not by way of limitation with regard to the claimed invention.

DETAILED DESCRIPTION OF ILLUSTRATIVE EMBODIMENTS

Figure 1:
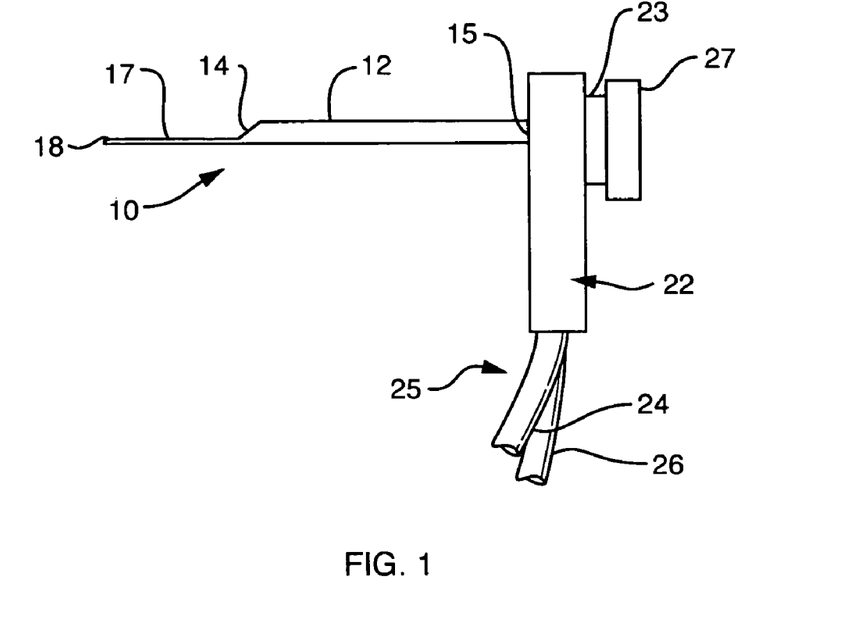
FIG. 1 is a schematic representation of a first ductal access device in accordance with one or more aspects of the present invention.
Figure 2:
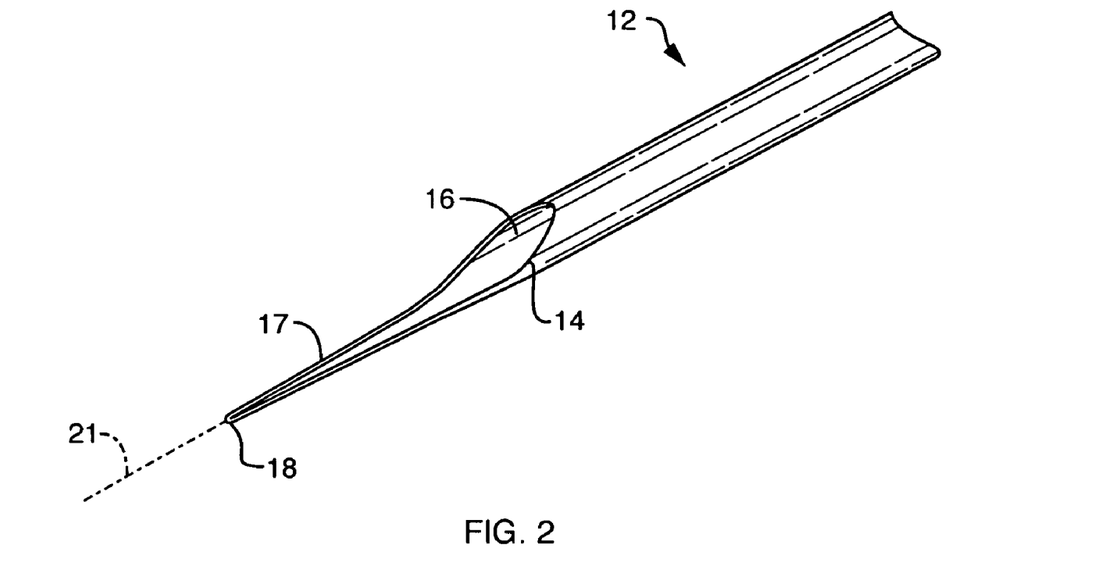
FIG. 2 is a perspective view of a catheter in accordance with one or more aspects of the present invention.
Figure 3:
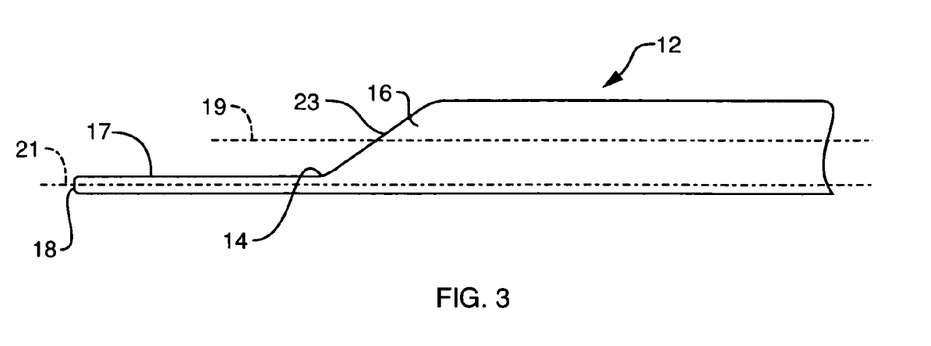
FIG. 3 is a partial schematic side view of a catheter in accordance with one or more aspects of the present invention.

FIGS. 1-3 illustrate preferred embodiments of an inventive access device 10 for accessing a body orifice, such as a breast duct. The access device 10 comprises a catheter 12 having a distal end 14 with a centrally disposed single lumen 16 which extends the length of the catheter 12, and an elongated distal tip portion 17 which extends beyond the distal end 14 a predetermined distance. The center axis 21 of distal tip portion 17 extends substantially parallel to the center axis 19 of single lumen 16 and is disposed within the wall of the catheter. In such an exemplary construction, the distal tip portion 17 is disposed "off-axis" or "off-center" from center axis 19 of lumen 16. The off-axis construction of distal tip portion 17 advantageously maintains the open inner diameter of the catheter for maximum fluid flow in and out of the breast duct. Further, the off axis configuration allows substantially improved flow because it does not to interfere with the introduction or removal of fluid and collected samples so not to compromise the ability to retrieve a meaningful sample while still being in direction of the catheter and lumen. The elongated configuration of the distal tip portion 17 acts as an effective guide while not interfering with fluid infusion or compromising ductal fluid sample collection. Distal tip portion 17 also provides ease of insertion of catheter 12 in the ductal orifice. In one construction, distal tip portion 17 is flexible in nature so as to allow the catheter to traverse the potentially tortuous and/or angled geometry of the human breast duct. Further, distal tip portion 17 distends the ductal orifice to reduce the associated pain upon insertion of the catheter therein.

Catheter 12 has dimensions which permit introduction of the distal end 14 through a ductal orifice and positioning a distal end thereof distal to the ductal sphincter of a human breast. In one construction, the catheter 12 has a maximum outer diameter of approximately 0.039 inches so as to cannulate the ductal orifices of the breast. Nevertheless, other dimensions are possible for the outer diameter(e.g., approximately 0.025 to 0.039 inches). Single lumen 16 with an internal ID of approximately 0.025 inches accesses the breast duct and through which fluid is infused, and from which ductal fluid samples including ductal epithelial cells are collected or drawn up out of the duct. Distal tip portion 17 has dimensions which permit introduction through a ductal orifice so as to lead the catheter 12 into the breast duct. In one exemplary construction, distal tip portion 17 has a smaller diameter than the catheter 12 to allow ease, of insertion into the breast duct. Distal tip portion 17 may have a diameter of approximately 0.010 inches, although, other dimensions are possible (e.g., 0.008 to 0.012 inches). In an alternative construction, the distal tip portion 17 may be flexible.

Referring to FIGS. 2 and 3, the distal tip portion 17 may have a tapered configuration being largest at the distal end 14 of the lumen 16 (i.e., proximal end of distal tip 17) extending therefrom to be smallest at the distal end 18. In use, the taper and flexibility of the distal tip portion 17 guides the catheter for intraductal movement. Shown in FIG. 3, the transition between the distal tip portion 17 and catheter 12 includes a beveled surface 23. This beveled surface 23 provides a smooth transition between distal tip portion 17 of catheter 12 which makes the catheter 12 easy to introduce into the ductal opening after the insertion of the tip portion 17 into the breast duct. Hence, the distal tip portion 17 may hold the duct opening in position so that the catheter 12 enters with relative ease. As may be appreciated by one of ordinary skill in the art, the beveled surface 23 reduces the stress level on the tissue being penetrated and spread open by the distal end 14 of the catheter 12. In contrast to traditional catheters, discomfort to the patient is greatly reduced with the access device 10 of the present invention. The edges of the catheter at the distal end and the end 18 of the distal tip 17 may include an atraumatic configuration. In one atraumatic configuration, the edges and end 18 are rounded to reduce friction and eliminate surfaces that could puncture or otherwise injure the duct. Thus, this construction reduces localized trauma to the tissue verses non-atraumatic designs.

Referring to FIG. 1, a multiport hub 22 is coupled to the proximal end 15 of catheter 12. In a preferred construction, hub 22 includes transparent material so that the user may visualize the flow to and from the breast duct during a lavage procedure. In another construction, hub 22 has a low profile so as to reduce the torque on the breast nipple after insertion of catheter 12. This overcomes the excessive generated torque on the breast nipple known to cause obstruction of ductal fluid due to compression of the tissue. Thus, improved collection of ductal cellular material is provided.

Hub 22 is attached to a tubing set 25 that comprises an infusion tube 24 from which fluid is infused into lumen 16 through hub 22 and a collection tube 26 from which fluid is collected from lumen 16 via hub 22. Infusion tube 24 and collection tube 26 are attached to hub 22 in a conventional manner to allow fluid flow. In one construction, infusion tube 24 and collection tube 26 are translucent and have standard luer connections at their distal ends that mate with ports on the hub 22 and receive fluids. The proximal ends of the tubes 24, 26 also include standard luer connection that a practitioner or attendant to manage the various ductal fluids using an appropriate syringe with a standard male luer. If desired, tubes 24, 26 may be labeled to indicate the inflow and outflow paths, e.g. infusion or collection functions.

In a further construction, an optional pinch clamp or other flow control device (not shown) may be disposed on the outflow tube, collection tube 26. In use, the clamp closes the collection tube 24 to prevent fluid leakage from the tubing during fluid infusion into a cannulated breast duct. In one construction, hub 22 includes an ergonomic handle 27 for the user to grasp during a ductal lavage procedure. It should be recognized that a fluid used in the hub 22 and catheter 12 may be virtually any appropriate fluid for the ductal lavage procedure. Exemplary ductal wash fluids which may be used with hub 22 includes but is not limited to saline, phosphate buffered saline, a nonabsorbable fluid, an isotonic solution, an osmotic solution, a hypotonic solution, and a hypertonic solution. Nevertheless, an appropriate therapeutic fluid may be provided by way of the ductal access devices describes herein. Alternatively, the fluids could include diagnostic or therapeutic fluids carrying diagnostic and/or therapeutic agents.

Figure 5:
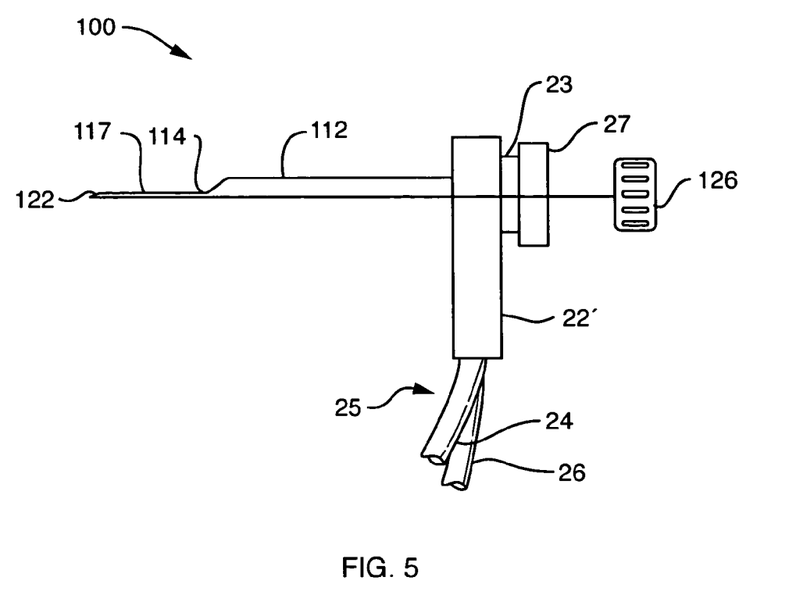
FIG. 5 is a schematic representation of a second ductal access device in accordance with one or more aspects of the present invention
Figure 6:
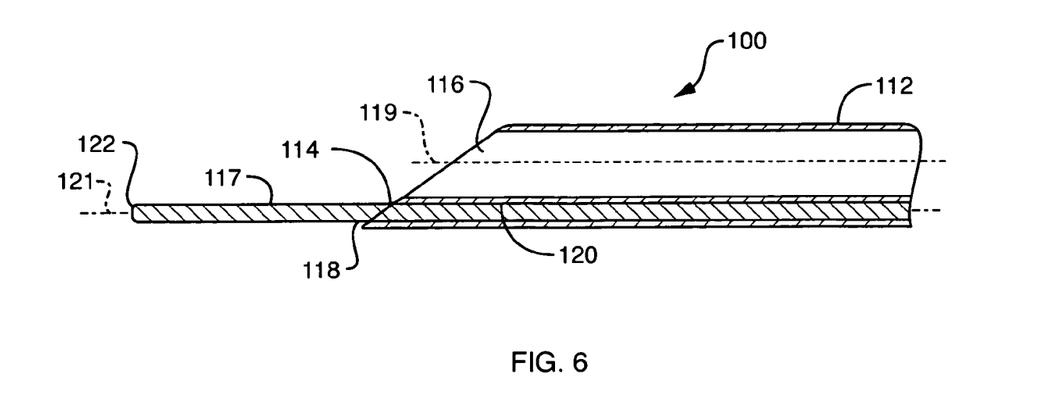
FIG. 6 is a sectional view of a catheter shown in FIG. 5 taken along an central axis to illustrate an interior construction and components in accordance with one or more aspects of the present invention.

In an alternative construction depicted in FIGS. 5 and 6, an inventive ductal access system 100, includes a catheter 112 having a distal end 114 with a centrally disposed single lumen 116 which extends the length of the catheter 112. Catheter 112 includes a tubular introducer pathway 120 adapted to slidably receive a ductal introducer 118 therein. Long axis 121 of pathway 120 is offset but substantially parallel to long axis 119 of lumen 116. For ease of explanation, as used herein the term "introducer" is defined to include guidewires, dilators, stylettes or portion of any of these that may be inserted within a passageway of a catheter or into the ductal orifice. Ductal introducer 118 is provided for ease of varying the length of tip portion 117 so as to improve intraductal travel of the catheter 112 within the breast duct and to reduce risk of puncturing the ductal wall and rupturing the breast duct. By removably inserting the ductal introducer 118 into the axis 121 of pathway 120, the user is able to choose an introducer having a desired stiffness for the particular patient. Additionally, this enables the practitioner or attendant to change the flexibility and stiffness of the introducer 118. The stiffness and flexibility may be a function of a material property and/or cross-sectional shape. One example of a material property that relates to flexibility is the modulus of elasticity. In another example, the cross-sectional shape of the introducer 118 may be circular, elliptical, oval or other shapes that provide predetermined stiffness in one or more directions. One of skill in the art would recognize these various shapes relate to a section modulus of the introducer 118. Therefore, it should be recognized that introducer pathway 120 may be virtually any appropriate cross-sectional shape to meet the cross-sectional shape of the introducer 118.

Ductal introducer 118 includes a distal end 122, which enters the breast duct. The opposing proximal end 124 of ductal introducer 118 includes a handle 126. Handle 126 provides ease of operation so that a user may grasp and manipulate the introducer 118 to access and navigate the breast duct anatomy. Ductal access device 100 includes a hub 22' which has similar construction and components as hub 22 shown in FIG. 1. In hub 22', the introducer pathway 120 extends through so that the introducer 118 may be inserted. The pathway may be a tube extending through the exterior of the hub 22' or the tube may be located on the outer surface of the hub. An adjustable tip portion 117 of introducer 118 is defined from the distal end 122 of ductal introducer 118 to the distal end portion 114 of catheter 112. In this configuration, the length of the tip portion 117 is selectively adjustable by the user for accessing and traversing the breast duct. In one aspect, ductal introducer 118 may be embodied as a guide wire which is easily inserted into pathway 120 and into the breast duct. In one construction shown in FIG. 6, the center axis 121 of introducer pathway 120 extends substantially parallel to the center axis 119 of single lumen 116. As discussed above, in such an exemplary construction, the introducer pathway 120 is disposed "off-axis" or "off-center" from center axis 119 of lumen 116. Thus, ductal introducer 118 with the off-axis construction of catheter 112 provides similar benefits as the ductal access device 10.

Figure 11:
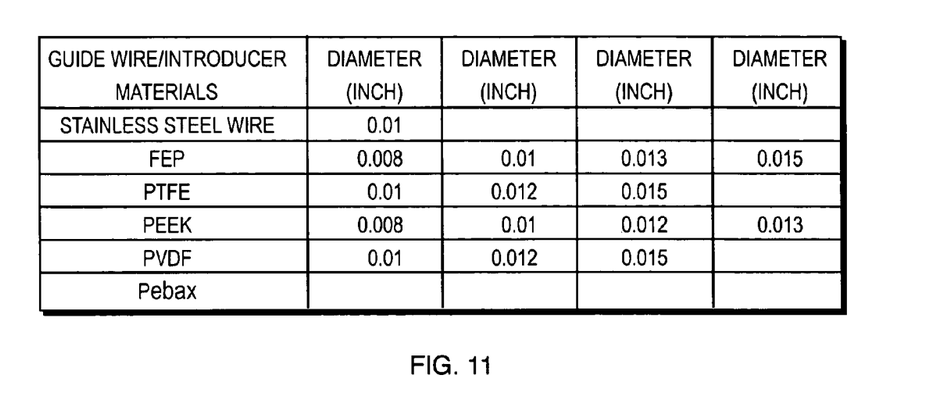
FIG. 11 is a table illustrating exemplary parametric values and materials for guide wire and introducers that may be implemented with aspects of the present invention.

The introducers described herein may be formed of appropriate cross-sectional shapes and various materials for medical use. The shapes and materials enable desired rigidity and flexibility for intraductal movement. Alternative materials for the introducer 118 may include but are not limited to: Stainless Steel Wire; FEP; PTFE; PEEK; and PVDF and PEBAX. Nevertheless, other appropriate materials may be employed. Specific dimensional value introducers are shown in FIG. 11, but are provided by way of example. Alternate coatings for the introducer and/or catheter may include but are not limited to: hydromer coating; STS SLIP-COAT; MDX; silicone dry; silicone lubricant; PTFE coatings. The specific thickness of the coatings and application may be readily determined by one of ordinary skill in the art.

The introducer may be made of metal or plastics and may have a tapered and/or an atraumatic tip for gently probing and accessing a breast duct. In one example, the introducer may be constructed of a superelastic or shape memory material. As used herein, the term "superelastic shape memory material" refers to a class of metal alloys that have a stress-induced phase change or temperate from austenite to martensite and upon stress release, the material springs back to this original phase and shape. The material structure of a superelastic shape memory material regarding austenite and martensite is well-known to one of ordinary skill in the metallurgy art. A NiTi material or NiTi alloy may be used as an alloy material for the introducer. As used herein, a NiTi superelastic shape memory material refers to an alloy that is an intermetallic compound of nickel and titanium having nearly equal mixtures as measured by weight. One composition of a NiTi superelastic shape memory material generally has a greater percentage of nickel by weight than titanium, such as 51%-

56% of nickel, and preferably 54-55% nickel. The specific percentages of nickel and titanium may be adjusted by one of ordinary skill in the art.

It is not necessary for the introducer to be composed of a material that has shape memory characteristics. The introducer may also be formed of a stiff material such as a metal wire or a flexible material such as plastic. In an embodiment of the invention, the combined introducer may be formed of Nitinol due to its flexibility, durability, and biocompatibility. In an alternative embodiment, the introducer may be formed of multiple materials or the same materials having different stiffnesses. As a result, the introducer may have sections that are more flexible than adjacent sections of the same introducer. As a result, for example, the introducer may have a first, stiff portion for guiding the introducer within the ductal lumen and a second, flexible portion that allows the introducer to conform to the shape of the ductal lumen or lumen branch into which it is introduced. In any of the above-discussed embodiments, the introducer may be coated with a liquid or dry lubricant material that reduces the friction between the introducer and the breast duct during the introduction and advancement of the introducer in the duct.

Figure 7:
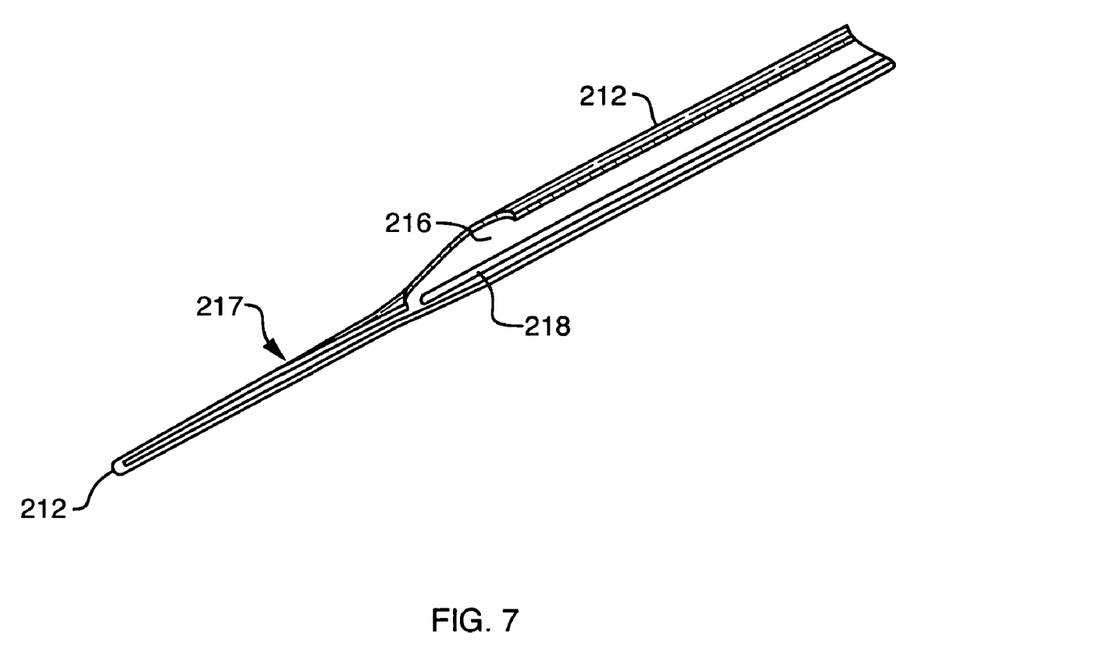
FIG. 7 is a perspective view of a catheter in accordance with one or more aspects of the present invention.
Figure 8:
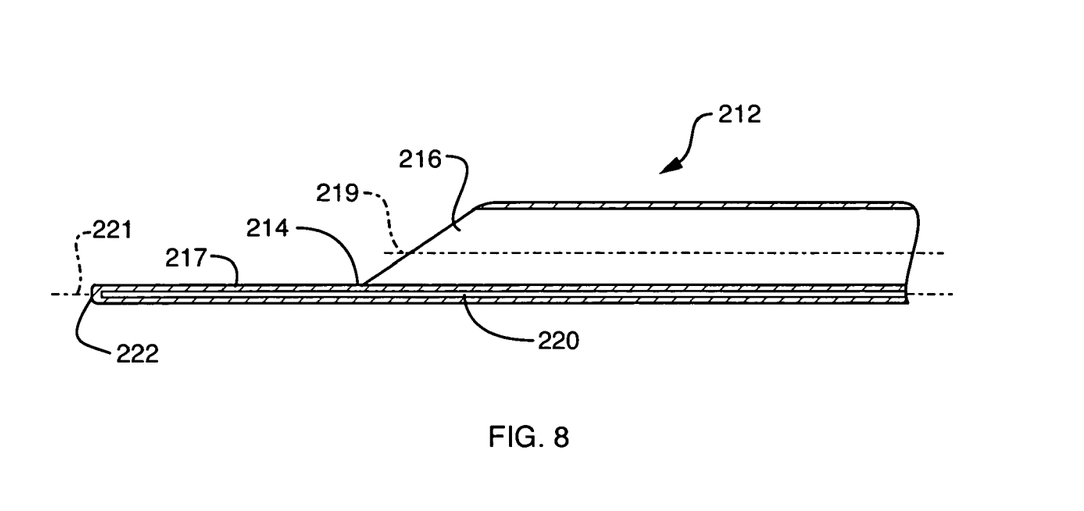
FIG. 8 is a sectional view of a catheter shown in FIG. 7 taken along an central axis to illustrate an interior construction and components in accordance with one or more aspects of the present invention.

FIGS. 7 and 8 illustrate an alternative construction of an inventive catheter body 212 having a distal end 214 with a centrally (about axis 219) disposed single lumen 216 that traverses the length of the catheter body. In an off-axis configuration, an elongated flexible tip 217 extends beyond the distal end 214 along axis 221. The tip 217 is configured to receive a removable introducer 218. This feature is achieved in that the tip 217 and catheter body 212 include an internal passageway 220 adapted to slidably receive the introducer 218. The passageway 220 may be tubular at the tip 217 and is located in the walls of catheter body 212. Passageway 220 has a closed distal end 122, which is in the initial portion that enters the breast duct. The passageway 220 is opened at the proximal end 211. The closed end feature enables the practitioner or user to adjust the flexibility of the distal 217 during cannulation of the breast duct but prevent fluid from entering the passageway 220. Further, the closed end feature allows the introducer 218 to be removed and another introducer inserted therein when the catheter 212 is positioned within the breast duct. Thus, introducer 218 may be removed or inserted into the tip 217 to selectively adjust the flexibility of tip 217. This allows the user to insert the introducer 218 making the flexible tip more rigid for insertion into the duct, or remove the stylette making the tip more flexible so the tip may transverse tortuous ductal geometry. In this configuration, passageway 220 extends the length of the lumen 216 and is parallel thereto. Advantageously, an aspect of the present invention provides an option to change to tip flexibility which greatly aids the cannulation of the breast duct. The material and thickness of flexible tip 217 may be chosen to achieve a desired stiffness in combination with the flexure characteristics of introducer 218. The closed distal end 222 is rounded to reduce friction between the ductal tissue and tip 217 and prevent the distal end 222 from puncturing duct.

Figure 8A:
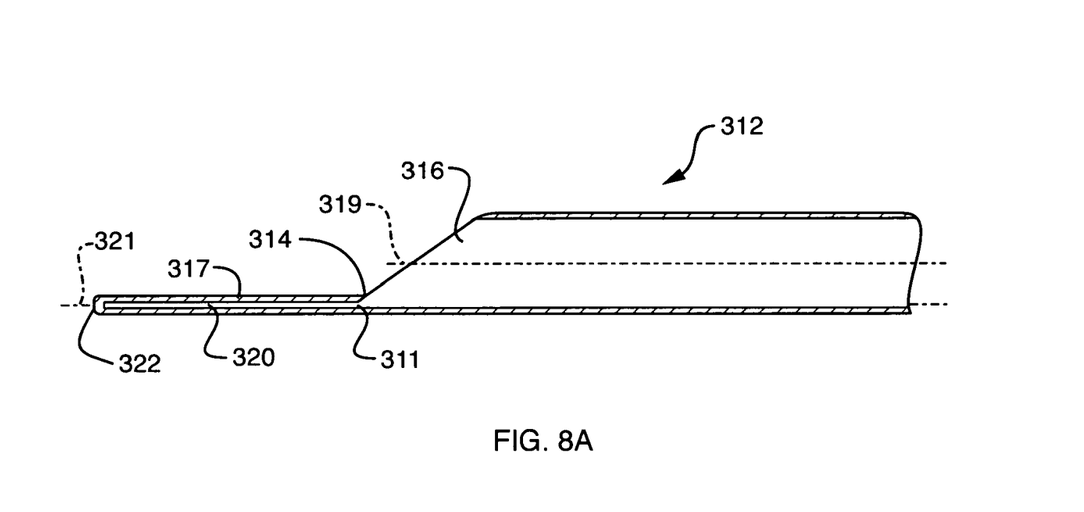
FIG. 8A is a sectional view similar to FIG. 8 showing an alterative embodiment of a catheter in accordance with one or more aspects of the present invention.

FIG. 8A illustrates an alternative catheter body 312, which has similar construction as catheter body 212 except that a passageway 320 is in the distal tip 317 and not in the walls of the catheter body 312. This allows the user to insert the introducer 218 through the lumen 316 and into the proximal end 311 of the passageway 320. Flexible elongated distal tip 317 includes a closed distal end 322 extending to the distal end 314 of catheter body 312.

In the example of the embodiments shown FIGS. 8 and 8A, the catheter 212, 312 may be provided with a plurality of introducers each of which have a different stiffness characteristic or property. Introducers are provided depending on the portion of duct being accessed. One introducer may be used to introduce the distal tip 217, 317 past the ductual sphincter. Another introducer may be provided to enter a desired branch of breast duct. Yet another introducer, if desired, may be used to enter a final portion of branch. This allows practitioner to design stiffness of tip 217, 317 to match needs presented by different portions of the duct.

An introducer may be designated with a stiffness value to provide a certain stiffness property relative to the other introducers. Purely by way of example, a practitioner may be provided with an introducer having a stiffness value of two which is designed to be rigid so as to allow penetrating the ductal opening. Another introducer may be provided having a stiffness value four which would be less stiff than a value of two. Yet another introducer may have a value of eight which would be less stiff than a value of four. In this example, a practitioner is enabled to access the breast duct with a rigid introducer inserted within the passageway 220, 320. The practitioner, while the catheter 212, 312 resides within the breast duct, may remove the rigid introducer and an insert another introducer to continue to advance within the breast duct. Thus, the practitioner is allowed to enter the breast with the catheters 212, 312 without removing the catheter once the breast duct is accessed. Advantageously, catheters 212, 312 allow the practitioner to be more efficient in the ductal access procedure because steps are eliminated or substantially reduced over conventional procedures, e.g, the use of dilators be significantly reduced. Further, patient comfort is increased because less traumatic movement is provided to the breast.

Figure 4:
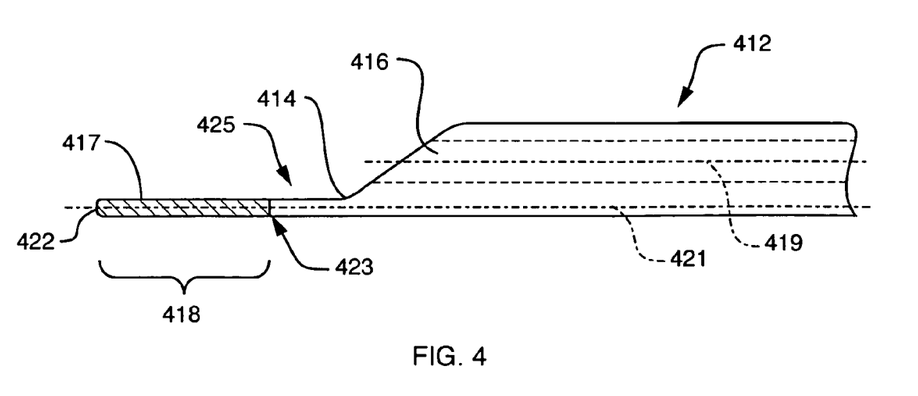
FIG. 4 is a schematic side view of a catheter with a removable tip in accordance with one or more aspects of the present invention.

In another construction shown in FIG. 4, a catheter 412 has a distal end 414 with a single lumen 416 disposed about a central axis 419 which extends the length of the catheter, and an elongated distal tip portion 417 which extends beyond the distal end 414. Catheter 412 has a bevel face and the tip portion 417 includes an extensible introducer 418 formed as a stylette portion. Stylette portion 418 comprises a distal end 422 extending from a distal opening 423 of a transition portion 425 of the lumen 416. Transition portion 425 includes a passageway configured to receive a stylette so that the distal end 422 exits the opening 433. The stylette portion 418 may be made of a flexible metal, plastic material or other materials described above. The stylette portion 418 may be fixed in position and serve as a flexible tip, or it may be removed after insertion of the catheter into the duct. The stylette portion 418 may be removed and replaced with a shorter stylette portion so as to shorten the tip length. Alternatively, the stylette portion 418 may have a longer length. In this manner, the tip length may be adjusted to accommodate the particular duct geometry.

Figure 13:
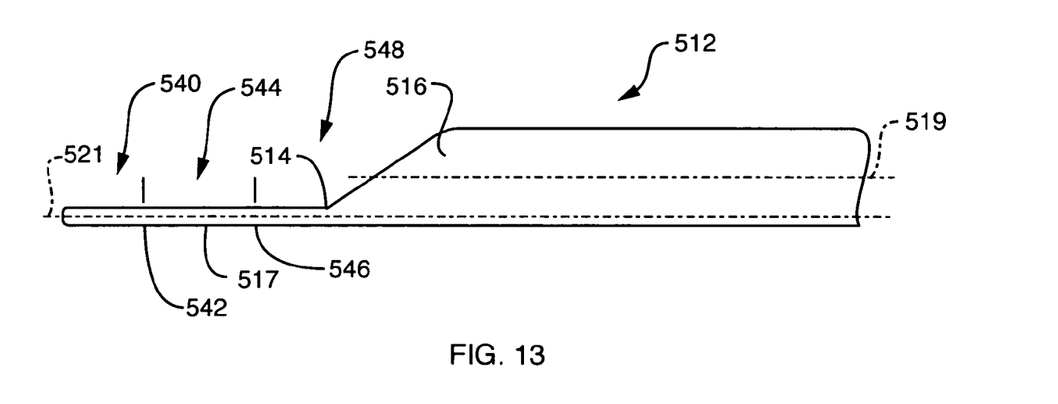
FIG. 13 is a partial schematic side view of a catheter in accordance with one or more aspects of the present invention.

FIG. 13 illustrates an alternative construction of an inventive catheter body 512 having a distal end 514 with a centrally (about axis 519) disposed single lumen 516 that traverses the length of the catheter body. In an off-axis configuration, an elongated tip 517 extends beyond the distal end 514 along axis 521. The elongated tip 517 may have a multi-flexion configuration that has separate regions of different flexions that each correspond to the flexibility, or lack thereof, needed to access a respective portion of a breast duct. This multi-flexion zone configuration provides adaptability for a practitioner to reduce steps for accessing a breast and/or customize the access of the duct to increase patient comfort. In one exemplary example, the elongated tip 517 may have three flex zones to accommodate to access a breast duct. A first flexion zone 540 may extend from the distal end to a first intermediate position 542 along the length of the elongated tip. The first flexion zone 540 maybe substantially rigid for entering into the breast duct to overcome the resistance force provided by the tissue at the ductal opening. An adjacent second flexion zone 544 may extend to another intennediate position away from first intermediate position 542 along the length of the elongated tip 517. The second flexion zone 544 may be less rigid than a first flex zone 544 so as to allow the elongated tip 517 to traverse the breast duct geometry. A third flex zone 548 may be provided adjacent to the second flexion zone 544. The third flexion zone 548 may be more flexible than the second flexion zone. In a specific example, the dimensions of the first flexion zone maybe 3 cm from the distal end; second flexion zone may have a length of 4 to 8 cm; and the third flexion own may have a length of 2 to 3 cm. Nevertheless, the length of the zones maybe configured as desired by the practitioner.

Figure 9A:
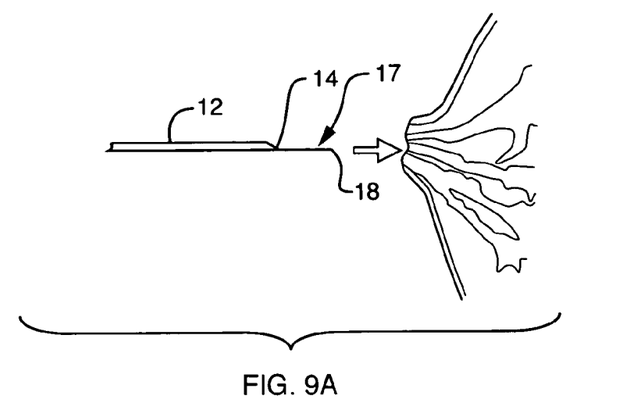
FIGS. 9A-9C are diagrams illustrating a method of accessing a breast duct which a catheter of FIG. 2.
Figure 9B:
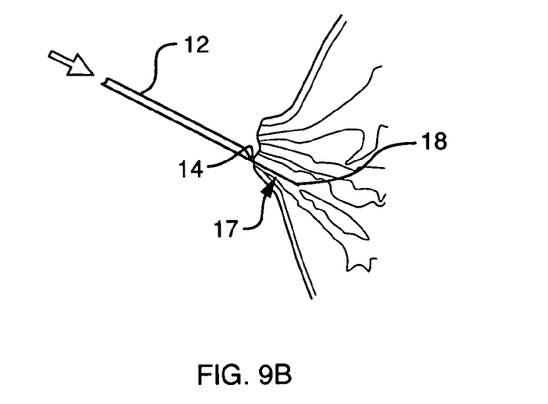
Figure 9C:
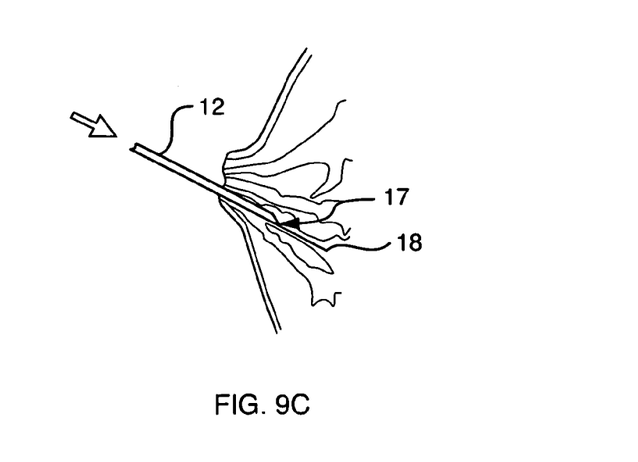

FIGS. 9A-9C are schematic diagrams illustrating a method of accessing a breast duct by way of a catheter 12 of FIG. 2. Referring to FIG. 9A, the catheter 12 is prepared to be introduced into a ductal orifice so that a distal end thereof will be positioned within the duct beyond the ductal sphincter during ductal lavage, introduction of diagnostic materials and/or introduction of therapeutic materials. As shown in FIG. 9B, the distal end 14 of the catheter is outside of the duct. The catheter has a flexible distal tip 17 which provides ease of insertion of catheter 12 in the ductal orifice. Further, the flexible distal tip 17 is inserted into the duct so as to follow the intraductal geometry but not cause damage to the duct. As shown in FIG. 9C, the distal end 14 has entered the duct. The distal tip 17 continues to follow the intraductal geometry to guide the catheter 12 therethrough. Further, the catheter 12 is more rigid than the distal tip 17 so as to straighten the duct for infusion and collection. Although catheter 12 is described with reference to FIGS. 9A-9C; other catheters 112, 212, 312, 412, and 512 may be used in a similar fashion.

Figure 10A:
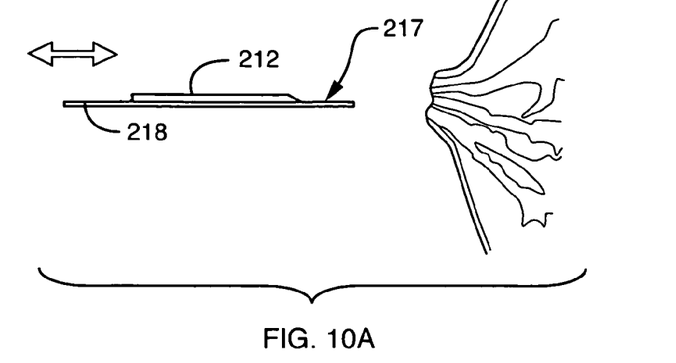
FIGS. 10A-10C are diagrams illustrating a method of accessing a breast duct which a catheter of FIG. 7.

FIGS. 10A-10C are schematic diagrams illustrating a method of accessing a breast duct with a catheter body 212 of FIG. 7. Referring to FIG. 10A, the catheter body 212 is prepared to be introduced into a ductal orifice. The practitioner may choose an introducer 218 of a desired flexibility or rigidity. For example, the introducer 218 of different rigidity properties may be inserted for adjusting to a desired tip characteristic during insertion of the distal tip 217 into the breast duct. This arrangement creates a composite insertion member for accessing the breast duct. The desired tip characteristic may relate to the stiffness and flexibility, which may be functions of a material property or a cross-sectional shape. One of skill in the art would recognize that the composite insertion member may have various shapes and material properties to vary the section modulus.

Figure 10B:
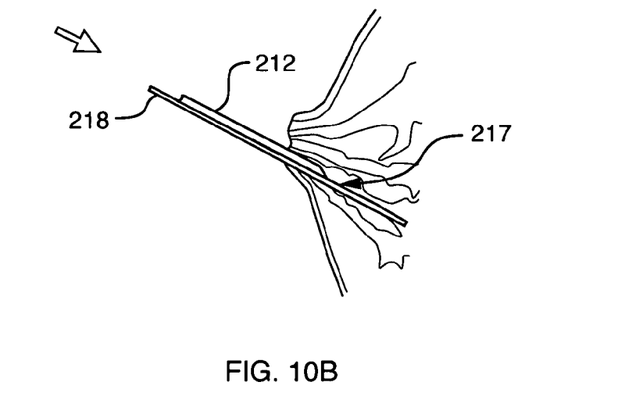
Figure 10C:
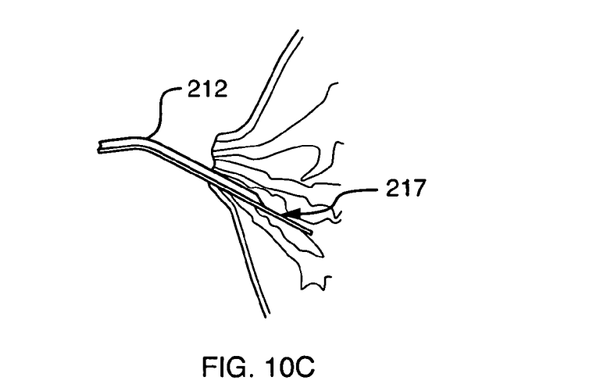

In particular, the tip 217 may be selectively made rigid to penetrate the duct orifice. In this configuration, the length of the catheter 212 and distal tip 217 is relatively rigid. In FIG. 10B, the introducer 218, which is rigid or somewhat rigid, has been removed from the distal tip 217 while the catheter 212 is inserted in the duct. In this removed configuration, the catheter 212 may flex and bend through the intraductal geometry. If desired, an introducer 218, which is less stiff, may be inserted into the distal tip 217. With or without an introducer 218, the catheter 212 is advanced further into the duct. In FIG. 10C, once a desired position is reached within the duct, a rigid or somewhat rigid introducer 218 may be inserted and advanced into the catheter 212 to straighten the duct for infuision and collection. In a shape memory embodiment, the stiffness or flexibility of introducer 218 may be adjusted in response to the addition of stimulus or removal of a stimulus without removal from the catheter 212. While not shown, it should be recognized that distal tip 217 could be inserted into the ductal orifice without the need of an introducer 218. The introducer of an appropriate stiffness may be inserted into the distal tip 217 during or after intraductal entry of the catheter 212. Although catheter 212 is described with reference to FIGS. 10A-10C, other catheters 112, 312, 412 and 512 may be used in a similar fashion.

Figure 12:
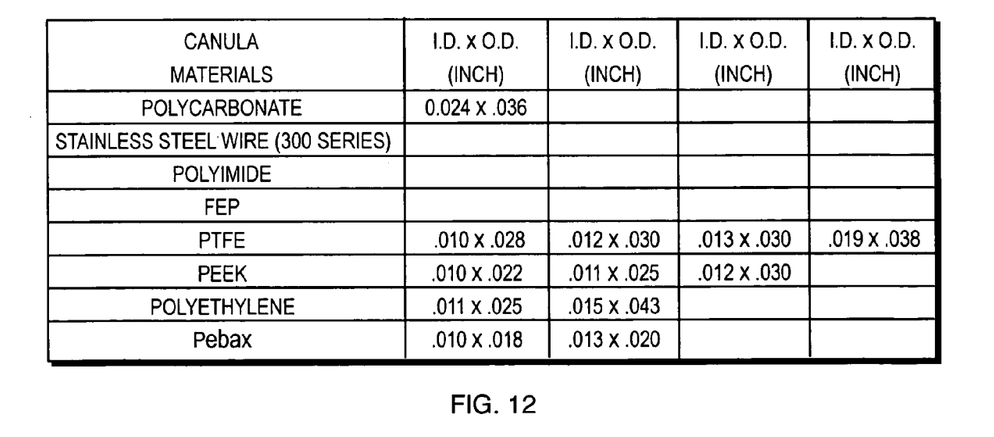
FIG. 12 is a table illustrating exemplary parametric values and materials for cannula that may be implemented with aspects of the present invention.

The catheters as described herein may be constructed of a wide range of appropriate materials for medical use. In a preferred construction, the catheter is formed with PTFE and coated with STS Slipcoat to reduce friction on the device during placement in the breast duct. In lieu of PTFE, alternate materials for the catheter may include but are not limited to: polycarbonate; stainless steel (300 Series); polymide; FEP; PEEK; polyethylene; and PEBAX. Specific dimensional values of catheters are shown in FIG. 12, but are provided by way of example. Nevertheless, other appropriate materials and dimensional values may be employed.

The hub 22 housing may be molded from a polycarbonate. The tubing set 25 may be made of PVC with luer connectors made of polycarbonate. The tubing set may be made of a variety of conventional materials including but not limited to: silicone; low density polyethylene; PVC; tygon; or polypropylene.

In one manufacturing process, the catheters according to one or more aspects of the present invention may be constructed by using an extrusion process. After the process, the distal end of catheter is shaped by molding and/or cutting. An optional, bevel may be is cut to provide the transition between the distal tip portion and the catheter. The edges of the catheter may be rounded using an RF tipping process known to one of ordinary skill in the art. The catheter may be bonded to the hub using a desired medical grade UV adhesive. In turn, the tubes may be bonded to the hub and to the luer connector using UV adhesive as well. If desired, a pinch clamp may be placed on the outflow tube.

The present invention provides a method for obtaining cellular material from a human breast milk duct includes introducing a ductal access device such as devices 12, 112, 212, 312, 412, and 512 having at least one lumen into a duct. A wash fluid may be introduced through the access device internal lumen into the milk duct. In the method, a volume of at least 2 ml of wash fluid may be present within the duct for a preselected time, and then at least a portion of the wash fluid is collected from the duct through the lumen of the access device. The method preferably further comprises massaging and squeezing the breast tissue after introducing the wash fluid but prior to and/or during collecting a portion of the wash fluid. Introducing the ductal access device typically comprises positioning a distal end of the catheter distal to the ductal sphincter in the breast duct. The access device preferably includes only a single lumen that extends into the duct. The preselected time may be less than one second, but will usually be in the range from one second to one hour.

Accordingly, there are any number of alternative combinations for defining the invention, which incorporate one or more elements from the specification, including the description, claims, and drawings, in various combinations or sub combinations. It will be apparent to those skilled in the relevant technology, in light of the present specification, that alternate combinations of aspects of the invention, either alone or in combination with one or more elements or steps defined herein, may be utilized as modifications or alterations of the invention or as part of the invention. It may be intended that the written description of the invention contained herein covers all such modifications and alterations.

The invention claimed is:

1. A ductal access device, comprising:
   an elongated member sized for positioning within a breast duct, said elongated member comprising an elongated internal lumen extending along a length of said elongated member and an elongated internal passageway extending along at least a portion of the length of the elongated member for receiving an introducer, said elongated member including a central longitudinal axis positioned and extending within the internal lumen and said elongated internal passageway including a centrally disposed longitudinal axis that is spaced from and offset from said central longitudinal axis; and
   said elongated member including an elongated distal tip extending beyond a distal end of the internal lumen and along said longitudinal axis of said elongated internal passageway and such elongated distal member includes a closed distal tip configured to abut a distal end of said introducer.

2. The ductal access device of claim 1, the elongated distal tip including said elongated internal passageway therein.

3. The ductal access device of claim 2, further comprising a multiport body attached to a proximal end of the internal lumen and communicating with said internal lumen for infusing fluid into the breast duct and for retrieving fluid from the breast duct.

4. The ductal access device of claim 1, in which said elongated distal tip includes a plurality of sections extending along a length each having a different stiffness.

5. The ductal access device of claim 1, in which the introducer includes a plurality of sections extending along a length thereof and each section having a different stiffness.

6. The ductal access device of claim 1, in which the elongated passageway is configured to receive a plurality of introducers of different predetermined lengths.

7. A ductal access device for accessing a breast duct, said device comprising:
   an elongated member comprising an internal lumen and being sized for positioning within the breast; said elongated member having a first centrally positioned axis extending through the internal lumen and a second axis being substantially parallel and offset relative to said first centrally positioned axis, said internal lumen having a distal end and an opposing proximal end;
   an elongated distal tip extending beyond said distal end of the internal lumen and along said second axis, said elongated distal tip having a closed distal end for navigating within the breast duct and an internal passageway sized to removably receive an elongated introducer therein; and
   a multiport body attached to the proximal end of the internal lumen and communicating with said lumen for infusing fluid into the breast duct and for retrieving fluid from the breast duct.

8. The device according to claim 7, in which the said passageway extends through said body.

9. The device according to claim 7, in which the said passageway extends within a wall of the elongated member to the proximal end of the lumen.

10. The device according to claim 7, in which the elongated distal tip extends from a wall of said lumen.

11. The device according to claim 7, further including a beveled surface being disposed between the distal end of the internal lumen and a proximal end of the elongated distal tip.

12. A ductal access system, said system, comprising:
   a cannula sized for positioning within the breast duct having an internal lumen; said cannula having a first axis extending through the internal lumen and a second axis being offset and substantially parallel to said first axis, said internal lumen having a distal end and an opposing proximal end,
   an elongated distal member extending beyond said distal end of the internal lumen and along said second axis, said elongated distal member including an internal passageway sized to slidiably receive an elongated introducer therein; and
   a multiport body attached to the proximal end of the internal lumen and communicating with said lumen for infusing fluid into the breast duct and for retrieving fluid from the breast duct, wherein said elongated distal member including an internal passageway extends through said body.

13. The system according to claim 12, in which the elongated distal member includes a closed distal tip configured to abut a distal end of said introducer.

14. The system according to claim 12, in which the elongated distal member includes an opened distal tip in which said introducer is extensible therethrough.

15. The system according to claim 12, in which the elongated distal member extends from a wall of said lumen.

16. The system according to claim 12, in which the introducer member is composed of a superelastic material.

17. The system according to claim 12, in which the elongated introducer includes a plurality of introducers each being of a different stiffness.

18. A method for obtaining cellular material from a human breast milk duct includes the steps of:
   providing the ductal access device of claim 1;
   inserting the introducer into the internal passageway of the elongated distal member to form a composite insertion member;
   inserting the composite insertion member into a ductal orifice of the breast duct;
   advancing the elongated member into the breast duct;
   and removing the introducer from the internal passageway.

19. A method for obtaining cellular material from a human breast milk duct includes the steps of:
   providing the ductal access device of claim 11;
   inserting the elongated distal member into a ductal orifice;
   inserting the introducer into the internal passageway of the elongated distal member to form a composite insertion member;
   advancing the composite insertion member and the internal lumen into the breast duct;
   and removing the introducer from the internal passageway.

* * * * *

UNITED STATES PATENT AND TRADEMARK OFFICE
CERTIFICATE OF CORRECTION

| | |
|---|---|
| PATENT NO. | : 7,494,472 B2 |
| APPLICATION NO. | : 10/746950 |
| DATED | : February 24, 2009 |
| INVENTOR(S) | : Sakal et al. |

It is certified that error appears in the above-identified patent and that said Letters Patent is hereby corrected as shown below:

In column 1, lines 59-67, below "cells." delete "Additionally, these techniques............... reference in its entirety." and insert the same after "cells." as continuation of the same paragraph.

In column 5, line 17, change "Infision" to --Infusion--.

In column 9, line 3, change "intennediate" to --intermediate--.

In column 9, line 62, change "infuision" to --infusion--.

Signed and Sealed this

Twenty-ninth Day of September, 2009

David J. Kappos
*Director of the United States Patent and Trademark Office*